US010265033B2

(12) United States Patent
Lim et al.

(10) Patent No.: US 10,265,033 B2
(45) Date of Patent: Apr. 23, 2019

(54) CT PHOTOGRAPHIC DEVICE COMPRISING A ROTARY DRIVING PART AND A LINEAR DRIVING PART

(71) Applicants: VATECH Co., Ltd., Gyeonggi-do (KR); VATECH EWOO Holdings Co., Ltd., Gyeonggi-do (KR)

(72) Inventors: Hyung Keun Lim, Gyeonggi-do (KR); Jin Pyo Chun, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 279 days.

(21) Appl. No.: 15/113,783

(22) PCT Filed: Jan. 26, 2015

(86) PCT No.: PCT/KR2015/000807
§ 371 (c)(1),
(2) Date: Jul. 22, 2016

(87) PCT Pub. No.: WO2015/111979
PCT Pub. Date: Jul. 30, 2015

(65) Prior Publication Data
US 2016/0345916 A1    Dec. 1, 2016

(30) Foreign Application Priority Data
Jan. 24, 2014   (KR) .................. 10-2014-0009244

(51) Int. Cl.
*A61B 6/03*   (2006.01)
*A61B 6/00*   (2006.01)
*A61B 6/14*   (2006.01)

(52) U.S. Cl.
CPC .............. *A61B 6/035* (2013.01); *A61B 6/032* (2013.01); *A61B 6/14* (2013.01); *A61B 6/4429* (2013.01);
(Continued)

(58) Field of Classification Search
CPC ........... A61B 6/032; A61B 6/035; A61B 6/14; A61B 6/501; A61B 6/4429; A61B 6/4435; A61B 6/4441
(Continued)

(56) References Cited

U.S. PATENT DOCUMENTS 5,214,686 A * 5/1993 Webber .................... A61B 6/14
378/147
6,055,292 A 4/2000 Zeller et al.
(Continued)

FOREIGN PATENT DOCUMENTS

EP  2198783 A1  6/2010
JP  10-243944 A  9/1998
(Continued)

OTHER PUBLICATIONS

European Patent Office, Extended European Search Report of corresponding EP Patent Application No. 15740403.9, dated Feb. 13, 2018.

*Primary Examiner* — Allen C. Ho
(74) *Attorney, Agent, or Firm* — IP Legal Services, LLC

(57) ABSTRACT

Disclosed is a dental X-ray CT photographic device. In order to resolve this issue, the CT photographic device according to the present invention comprises: a column; a first facing part which is disposed oriented towards an object to be examined on one side of the column, and comprises one or other of an X-ray generator and an X-ray sensor; a rotational arm coupled in such a way as to be able to rotate through at least a predetermined angular range with respect to the
(Continued)

column; and a second facing part which is disposed on the rotating arm, on the far side from the column, facing the first facing part with the object to be examined placed in between, and which comprises the other of an X-ray generator and an X-ray sensor.

8 Claims, 6 Drawing Sheets

(52) U.S. Cl.
CPC .......... *A61B 6/4435* (2013.01); *A61B 6/4441* (2013.01); *A61B 6/4458* (2013.01); *A61B 6/501* (2013.01)

(58) Field of Classification Search
USPC .......... 378/17, 20, 38–40, 19, 189, 191, 196, 378/197
See application file for complete search history.

(56) References Cited

U.S. PATENT DOCUMENTS

| | | | | |
|---|---|---|---|---|
| 6,173,035 B1 * | 1/2001 | Tachibana | ................ | A61B 6/14 378/39 |
| 6,289,074 B1 * | 9/2001 | Arai | ................ | A61B 6/032 378/38 |
| 6,493,415 B1 * | 12/2002 | Arai | ................ | A61B 6/14 378/38 |
| 6,496,558 B2 * | 12/2002 | Graumann | ................ | A61B 6/0478 378/197 |
| 6,940,941 B2 * | 9/2005 | Gregerson | ................ | A61B 6/032 250/363.05 |
| 6,990,174 B2 * | 1/2006 | Eskelinen | ................ | A61B 6/032 378/38 |
| 7,099,430 B2 * | 8/2006 | Müller | ................ | A61B 6/032 378/19 |
| 7,108,421 B2 * | 9/2006 | Gregerson | ................ | A61B 6/032 378/197 |
| 7,110,487 B2 * | 9/2006 | Baba | ................ | A61B 6/466 378/11 |
| 7,188,998 B2 * | 3/2007 | Gregerson | ................ | A61B 6/02 378/197 |
| 7,269,242 B2 * | 9/2007 | Tanaka | ................ | A61B 6/0478 378/16 |
| 7,322,746 B2 * | 1/2008 | Beckhaus | ................ | A61B 6/032 378/19 |
| 7,418,074 B2 * | 8/2008 | Du | ................ | A61B 6/032 378/13 |
| 7,486,759 B2 * | 2/2009 | Suzuki | ................ | A61B 6/14 378/38 |
| 7,515,679 B2 * | 4/2009 | Tacconi | ................ | A61B 6/032 378/15 |
| 7,577,232 B2 * | 8/2009 | Tachibana | ................ | A61B 6/14 378/116 |
| 7,711,085 B2 * | 5/2010 | Suzuki | ................ | A61B 6/14 378/39 |
| 7,787,586 B2 * | 8/2010 | Yoshimura | ................ | A61B 6/032 378/38 |
| 7,798,708 B2 * | 9/2010 | Erhardt | ................ | A61B 6/032 250/370.09 |
| 7,804,933 B2 | 9/2010 | Nyholm | | |
| 7,852,981 B2 * | 12/2010 | Luo | ................ | A61B 6/032 250/370.09 |
| 7,945,016 B2 * | 5/2011 | Bothorel | ................ | A61B 6/14 378/148 |
| 7,991,107 B2 * | 8/2011 | Sadakane | ................ | A61B 6/14 378/39 |
| 8,005,186 B2 * | 8/2011 | Lee | ................ | A61B 6/032 378/13 |
| 8,005,187 B2 * | 8/2011 | Suzuki | ................ | A61B 6/032 378/19 |
| 8,306,182 B2 * | 11/2012 | Yaoi | ................ | A61B 6/035 250/370.09 |
| 8,363,780 B2 * | 1/2013 | Loustauneau | .......... | A61B 6/587 378/13 |
| 8,433,033 B2 * | 4/2013 | Harata | ................ | A61B 6/583 378/38 |
| 8,503,603 B2 * | 8/2013 | Tancredi | ............... | A61B 6/0478 378/39 |
| 8,503,604 B2 * | 8/2013 | Inglese | ................ | A61B 6/14 378/19 |
| 8,525,833 B2 * | 9/2013 | Papaioannou | .......... | A61B 6/04 345/419 |
| 8,588,364 B2 * | 11/2013 | Suzuki | ................ | A61B 6/14 378/38 |
| 8,727,617 B2 * | 5/2014 | Augais | ................ | A61B 6/145 378/168 |
| 8,817,944 B2 * | 8/2014 | Arai | ................ | A61B 6/06 378/11 |
| 9,036,775 B2 * | 5/2015 | Yoshikawa | ............. | A61B 6/145 378/38 |
| 9,036,776 B2 * | 5/2015 | Sadakane | ............... | A61B 6/145 378/38 |
| 9,084,568 B2 * | 7/2015 | Katsumata | ............... | A61B 6/14 |
| 9,119,575 B2 * | 9/2015 | Sadakane | ................ | A61B 6/03 |
| 9,161,729 B2 * | 10/2015 | Hsieh | ................ | A61B 6/06 |
| 9,200,948 B2 * | 12/2015 | Jan | ................ | A61B 6/035 |
| 9,299,190 B2 * | 3/2016 | Koivisto | ............... | A61B 5/0064 |
| 9,532,753 B2 * | 1/2017 | Kim | ................ | A61B 6/032 |
| 9,668,705 B2 * | 6/2017 | Yamakawa | ............. | A61B 6/14 |
| 9,974,493 B2 * | 5/2018 | Kim | ................ | A61B 6/032 |
| 2005/0129173 A1 | 6/2005 | Eskelinen | | |
| 2008/0298554 A1 | 12/2008 | Tacconi et al. | | |
| 2009/0168966 A1 | 7/2009 | Suzuki et al. | | |
| 2015/0305696 A1 | 10/2015 | Yamakawa et al. | | |

FOREIGN PATENT DOCUMENTS

JP 4567064 B2 10/2010
WO 2012/008492 A1 1/2012

* cited by examiner

CT PHOTOGRAPHIC DEVICE COMPRISING A ROTARY DRIVING PART AND A LINEAR DRIVING PART

CROSS REFERENCE TO RELATED APPLICATIONS

This application is a National Stage Patent Application of PCT International Patent Application No. PCT/KR2015/000807 (filed on Jan. 26, 2015) under 35 U.S.C. § 371, which claims priority to Korean Patent Application No. 10-2014-0009244 (filed on Jan. 24, 2014), the teachings of which are incorporated herein in their entireties by reference.

TECHNICAL FIELD

The present invention relates generally to a computed tomography (CT) radiography device and, more particularly, to a computed tomography (CT) radiography device for dental clinics in which a patient's head including teeth is used as a major subject.

BACKGROUND ART

In the medical field, an X-ray radiography device refers to a device in which a predetermined amount of X-rays are transmitted to a desired body part and an X-ray sensor provides an image by using electrical signals generated by receiving the transmitted X-ray. The X-rays transmitted through the body part generate different electrical signals according to a damping ratio of the X-rays at each point of the body part being captured, and an image is implemented by using such electrical signals and position information.

In the field of dentistry, an X-ray computed tomography (CT) radiography device refers to a device that provides a three dimensional image including tomography information thereof by rotating relative to a major target among body parts of a patient such as teeth, a temporomandibular joint or the entire head and reconfiguring radiographs obtained at various angles.

In a conventional CT radiography device for dental clinics, an X-ray generator is provided on a first side of a rotation arm, the rotation arm is provided to rotate on a rotation axis which is perpendicular to the ground according to a direction of a longitudinal axis of a patient, and an X-ray sensor is installed to face the X-ray generator. The patient is positioned between the X-ray generator and the X-ray sensor and the rotation arm rotates on the rotation axis, and multiple radiographs are obtained by rotating the X-ray generator and the X-ray sensor near a dental arch at a certain height. Generally, the X-ray sensor rotates on a rotation axis with a turning radius that is relatively close to the rotation axis, and the X-ray generator rotates with a turning radius that is relatively far away from the rotation axis. Thus, a wider space than the actual size of the device is required to install the device since the maximum turning radius within the entire rotating section should be considered.

In addition, a conventional CT radiography device for dental clinics includes a rotation arm, in which an X-ray generator and an X-ray sensor are connected to both ends of the rotation arm, respectively, and the rotation arm is connected to a column which is stood perpendicular to the ground, through a supporting part of the rotation arm. The supporting part of the rotation arm not only holds the weight of the X-ray generator, the X-ray sensor, and the rotation arm, but also a driving part that drives the rotation arm. Therefore, much effort is required when designing and manufacturing of the supporting part of the rotation arm. Further, additional effort and cost are required on designing when manufacturing the column and a base support thereof since a center of gravity of the rotation arm is located outside of the column.

DETAILED DESCRIPTION OF THE INVENTION

Technical Problem

Accordingly, the present invention is intended to propose a CT radiography device in which a space required for a rotation of an X-ray generator is reduced when radiographing. Therefore, the device can be installed in smaller space. Also, the present invention is also intended to propose a CT radiography device in which a design and a production method are simplified and mechanical reliability of the device is realized when providing such CT radiography device.

Technical Solution

In order to achieve the above object, a CT radiograph device according to the present invention may include a column; a first facing part provided on a first side of the column to face a subject and including one of an X-ray generator and an X-ray sensor; a rotation arm connected to the column and configured to rotate relative to the subject within at least a predetermined angular range; and a second facing part provided on a first end of the rotation arm to face the first facing part with the subject being interposed between the first and second facing parts, and including a remaining one of the X-ray generator and the X-ray sensor.

The X-ray generator and the X-ray sensor may be placed to arrange at least a part of the X-ray sensor facing the X-ray generator with the subject being interposed therebetween within an X-ray irradiation range of the X-ray generator, while the rotation arm is placed within the predetermined angular range.

The X-ray sensor may be provided on the first facing part and the X-ray generator may be provided on the second facing part. In this case, the X-ray sensor may move within the first facing part along a rotational direction of the rotation arm such that at least a part of the X-ray sensor faces the X-ray generator within an X-ray irradiation range of the X-ray generator, with the subject being interposed therebetween.

The X-ray sensor may move along tracks having various shapes within the first facing part. In one embodiment, the X-ray sensor may move along a track having a constant distance from the subject. In other embodiment, the X-ray sensor may move along a track having a constant distance from the X-ray generator. In another embodiment, the X-ray sensor may move along a track that has a constant ratio of a distance between the X-ray generator and the subject and a distance between the X-ray generator and the X-ray sensor.

Meanwhile, the X-ray sensor may be a curved sensor configured to place at least a part of the X-ray sensor facing the X-ray generator, with the subject being interposed therebetween within a rotation angular range of the rotation arm.

The CT radiograph device according to the present invention may further include a first driving part reciprocally rotating the second facing part within a predetermined angular range; and a second driving part simultaneously or alternatively operated with the first driving part and moving at least one of the first facing part and the second facing part in a direction of a longitudinal axis of the subject. In this case, the first driving part may a rotary driving part connecting the column and the rotation arm and rotates the rotation arm on an axis of the column, and the second driving part may a linear driving part lifting and lowering at least one of the first facing part and the second facing part relative to the column.

Advantageous Effects

According to the present invention, a space required for a rotation is reduced by reciprocally moving an X-ray generator and an X-ray sensor within a certain angular range while radiographing, and a proper scanning method is applied to obtain radiographs in the reduced space. Therefore, a CT radiography device that can be installed in smaller space is provided. When providing such a CT radiography device, the present invention provides a simplified design and a production method in which the X-ray generator and the X-ray sensor are connected to the column such that they are properly operated in the reduced space. Accordingly, there is an effect of providing a CT radiography device with improved mechanical reliability.

MODES FOR CARRYING OUT THE INVENTION

Figure 1:
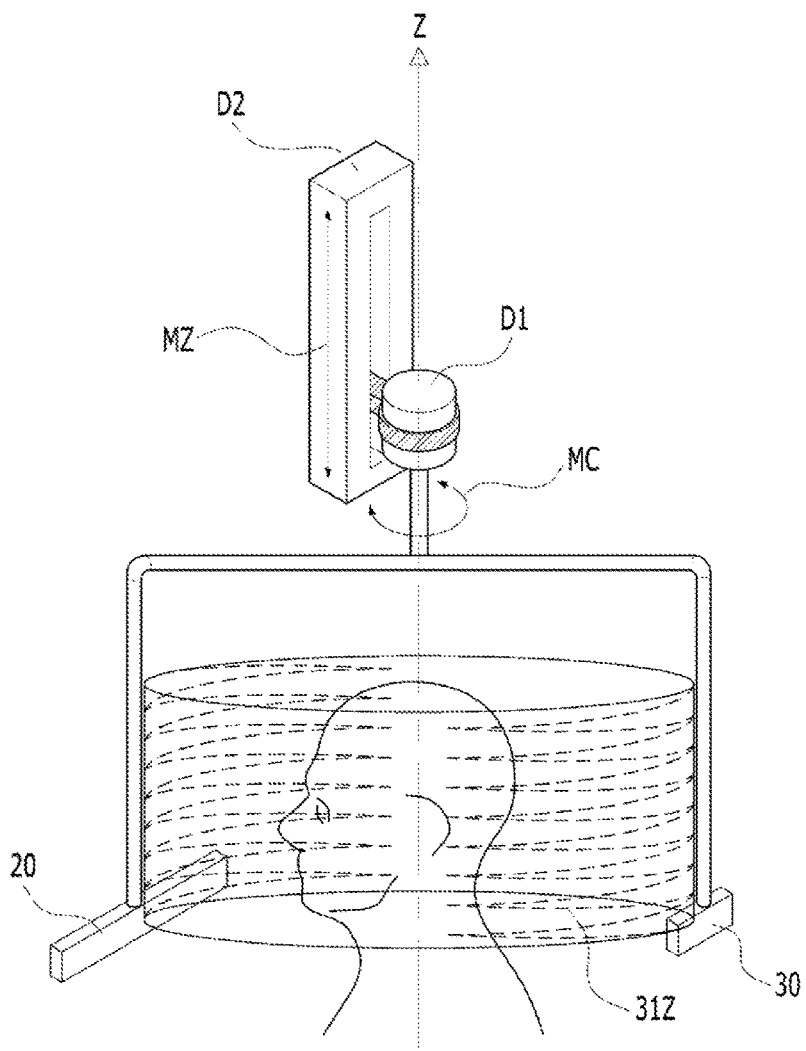
FIG. 1 is a schematic diagram showing a track of a CT radiography device according to an embodiment of the present invention.

Reference will now be made in greater detail to an exemplary embodiment of the present invention, an example of which is illustrated in the accompanying drawings. Wherever possible, the same reference numerals will be used throughout the drawings and the description to refer to the same or like parts.

FIG. 1 is a schematic diagram showing a track of a CT radiography device according to an embodiment of the present invention. As shown in the figure, an X-ray sensor 20 and an X-ray generator 30 are provided to face each other with a subject being interposed between the X-ray sensor 20 and an X-ray generator 30.

As shown in the embodiment of FIG. 1, the X-ray sensor 20 and the X-ray generator 30 are maintained to face each other and scan the subject while forming a zigzag track 31z within a predetermined angular range while maintaining the subject interposed therebetween.

In FIG. 1, for the sake of convenience, the rotation axis of each of the X-ray sensor 20 and the X-ray generator 30 is shown as parallel to the longitudinal axis Z of the subject. However, a direction of a rotation axis of a CT radiography device according to the embodiment of the present invention may be the same as the FIG. 1, or may have a predetermined angle relative to the longitudinal axis Z of the subject. In addition, as shown in FIG. 1, the rotation axis may be placed between the X-ray sensor 20 and the X-ray generator 30, in the X-ray sensor 20, or in the X-ray generator 30.

In the CT radiography device according to the present invention, the X-ray sensor 20 and the X-ray generator 30 reciprocally rotate within a predetermined angular range and the X-ray sensor 20 and the X-ray generator 30 move in a direction of the longitudinal axis Z. Other examples may be readily understood to a person of ordinary skills in the art through the following description. For example, the reciprocal rotation of the X-ray sensor 20 and the X-ray generator 30 may be understood to include all operations in which the X-ray sensor 20 receives an X-ray beam having been transmitted through the subject. A rotational motion MC is applied to at least one of the X-ray sensor 20 and the X-ray generator 30 relative to the longitudinal axis Z by a first driving part D1, and the X-ray beam transmits through the subject. In the same manner as a sensor used in a panoramic radiography device for dental clinics, the X-ray sensor 20 may be a bar type sensor that is rotated at 90 degrees from an angle that is set when radiographing a panoramic image to be perpendicular to the longitudinal axis Z of the subject. In addition, the X-ray sensor 20 may be a sensor having a large size such that the sensor may correspond to the X-ray generator 30 of a cone beam type. Various sensors may be used for the X-ray sensor 20 including a sensor obtaining radiograph information of a single slice and a sensor having various aspect ratios and being capable of obtaining multiple slices such as Multiple Detector Computed Tomography (MDCT). The X-ray sensor 20 may be a curved sensor in which a part facing the subject has a concave shape.

The X-ray generator 30 is an X-ray source, and the X-ray source may emit a collimated X-ray beam in the shape of the X-ray sensor 20.

The first driving part D1 may be configured to rotate the X-ray sensor 20 and the X-ray generator 30 such that an irradiation direction of an X-ray beam and/or a receiving direction of an X-ray beam are rotated on the longitudinal axis Z of the subject. Herein, the first driving part D1 may be configured to move at least one of the X-ray sensor 20 and the X-ray generator 30, or to separately move the X-ray sensor 20 and the X-ray generator 30. The first driving part D1 is configured to move the irradiation direction of the X-ray beam or the receiving direction of the X-ray beam of the subject by reciprocally rotating the X-ray sensor 20 and the X-ray generator 30, and to maintain a relative positional relationship in which the X-ray sensor 20 and the X-ray generator 30 face each other.

The CT radiography device according to the present invention may further include a second driving part D2 that moves a rotation arm of the CT radiography device for dental clinics or a corresponding structure thereof in a direction of the longitudinal axis MZ of the subject. The second driving part D2 may be configured to move a structure that guides each of the X-ray sensor 20 and the X-ray generator 30 to the direction of the longitudinal axis MZ of the subject. The detailed configuration thereof is described later and the configuration may be embodied in various forms including the disclosed embodiment.

The predetermined angular range may be predetermined according to a reconfiguration method of CT images and a characteristic of the device, and may be adjusted within a maximum predetermined range according to an object of CT radiography or a characteristic of the subject. However, the maximum predetermined range may be less than 360 degrees, or from 30 degrees to 90 degrees.

Figure 2:
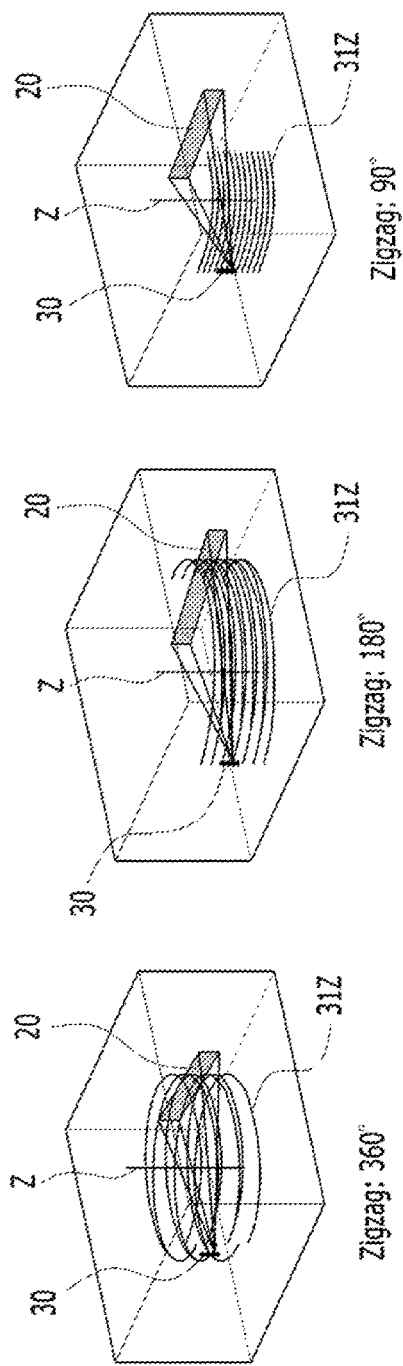
FIG. 2 is a schematic diagram showing various tracks in which various angular ranges are applied to the CT radiography device of the embodiment of FIG. 1.

FIG. 2 is a schematic diagram showing various zigzag tracks 31Z in which various angular ranges are applied to the CT radiography device of the embodiment of FIG. 1. A zigzag track 31Z displayed in the present figure is based on a position of the X-ray generator 30. A zigzag track 31Z with 360 degrees, 180 degrees, 90 degrees, or an angle within a certain angular range from 90 to 360 degrees may be formed according to an angular range of a partial reciprocal rotation that is performed by the first driving part D1 as described above.

Meanwhile, the zigzag track 31Z shown in FIGS. 1 and 2 is formed by simultaneously operating the first driving part D1 and the second driving part D2, and then a point, in which a direction of reciprocal rotation is changed, appears such that the zigzag tracks 31Z is bent in a shape of "Z". Alternatively, when the first driving part D1 and the second driving part D2 are alternatively operated, then the point, in which the direction of reciprocal rotation is changed, appears such that the zigzag tracks 31Z is bent in a shape of "ㄹ".

Figure 3:
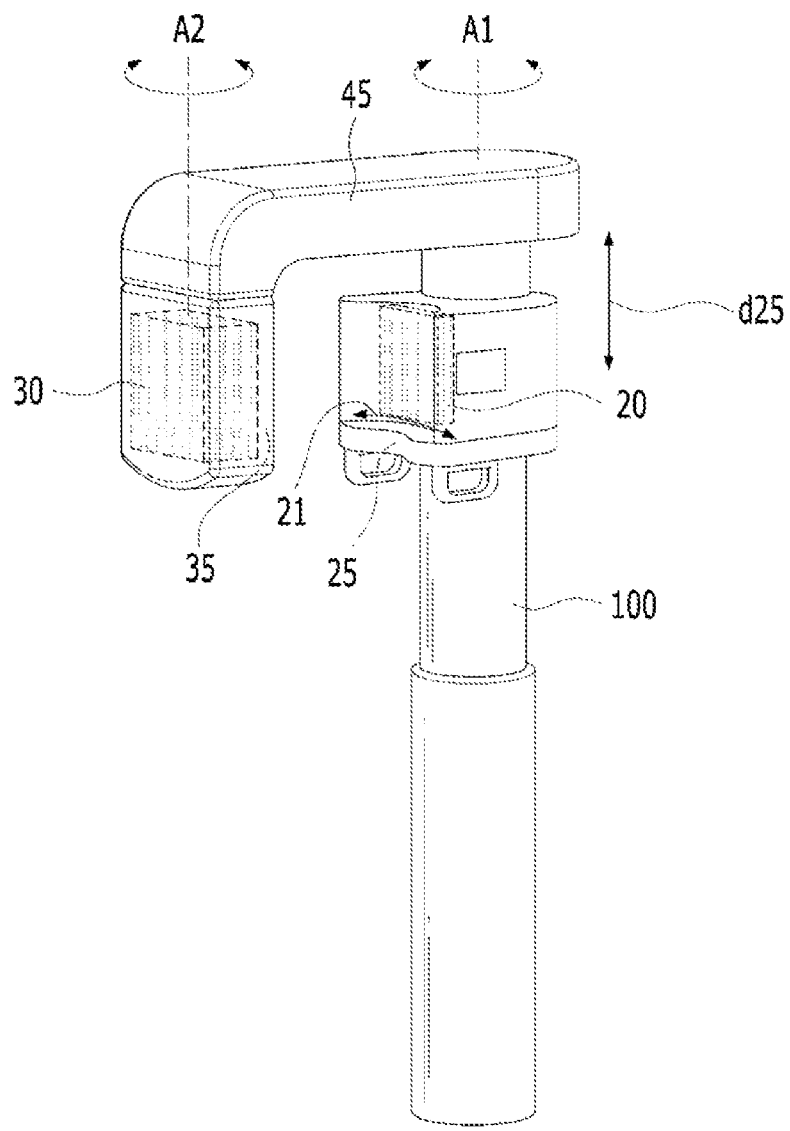
FIG. 3 is a perspective view of a CT radiography device according to an embodiment of the present invention.

FIG. 3 is a perspective view of a CT radiography device according to an embodiment of the present invention. A CT radiography device according to an embodiment of the present invention includes a column 100 installed to be fixed on the floor, a first facing part 25 that is provided on a first side of the column 100 to face a subject and includes an X-ray sensor 20, a rotation arm 45 that is connected to the column 100 such that the rotation arm 45 is able to rotate relative to the column 100 within at least a predetermined angular range, and a second facing part 35 that is provided on a far side of the column 100 to face the first facing part 25 with the subject being interposed therebetween and includes an X-ray generator 30.

The CT radiography device according to the embodiment connects the rotation arm 45 and the column 100, and further includes a rotary driving part that rotates the rotation arm 45 relative to a rotation axis A1 of the column 100, and a linear driving part (not shown) that moves the first facing part 25 to a length direction d25 of the column 100. Meanwhile, the linear driving part simultaneously moves the rotation arm 45 and the first facing part 25 such that the X-ray generator 30 of the second facing part 35 and the X-ray sensor 20 of the first facing part 25 may move in a direction of a longitudinal axis Z of the subject (Herein, parallel to the length direction of the column 100).

The X-ray sensor 20 may be installed to move along a certain track 21 within the first facing part 25. For example, the X-ray sensor 20 may be installed to be interlocked with a rotation of the rotation arm 45, to move along a rail or a track 21 provided on a case of the first facing part 25 and to face the X-ray generator 30.

A structure, for example, a bite-block, a headrest, a temple support, etc. may be installed to fix a patient's head. Meanwhile, the second facing part 35 including the X-ray generator 30 may be installed to rotate on a rotation axis A2.

When the second facing part 35 is fixed to a body of the rotation arm 45 and a center of an X-ray beam emitted from the X-ray generator 30 is always directed toward the rotation axis A1 of the rotation arm 45, then, the center of the X-ray beam may be directed away the subject and the X-ray sensor 20. However, if an irradiation range of the X-ray beam does not bound the subject and the X-ray sensor 20, then, a reciprocal rotation of the rotation arm 45 is available. In addition, if the second facing part 35 separately rotates from the body of the column 100, the second facing part 35 may rotate on the rotation axis A2 such that the X-ray beam emitted from the X-ray generator 30 may be directed toward the subject according to the rotation of the rotation arm 45.

In the present embodiment, the first driving part D1 described above corresponds to the rotary driving part that rotates the rotation arm 45 and mechanical elements that are interlocked with the driving part, and move or rotate the X-ray generator 30 and the X-ray sensor 20 such that the X-ray generator 30 and the X-ray sensor 20 face each. Further, the second driving part D1 corresponds to mechanical elements that move the X-ray generator 30 and the X-ray sensor 20 to the direction of the longitudinal axis Z of the subject, and the detailed configuration can be variously modified differently than disclosed in the embodiment.

Figure 4:
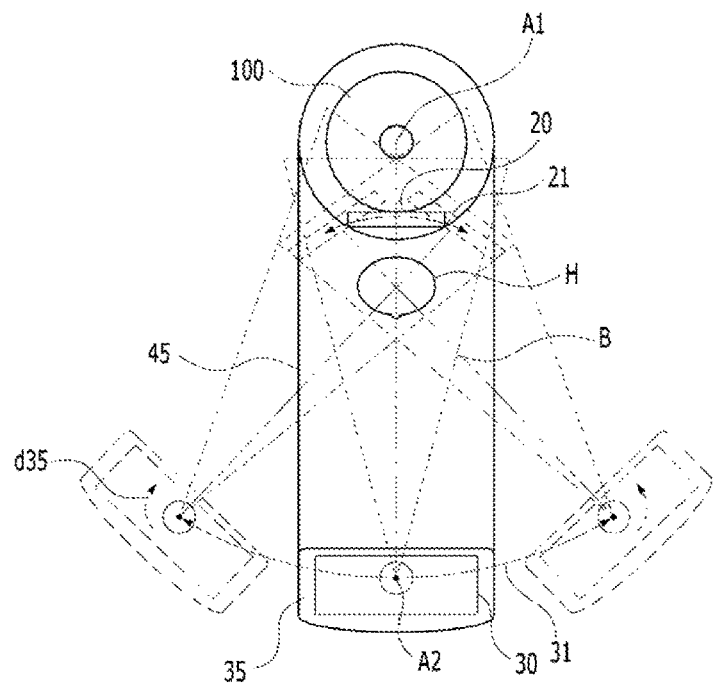
FIG. 4 is a schematic diagram showing a part of a track of the CT radiography device according to the embodiment of FIG. 3.

FIG. 4 is a schematic diagram showing a part of a track of the CT radiography device according to the embodiment of FIG. 3. According to the present figure, a track 21 of the X-ray sensor 20, a track 31 of the X-ray generator 30, and a location relation of the tracks and the subject H are displayed. As described above, the X-ray sensor 20 may be installed to be interlocked with the rotation of the rotation arm 45 and to move along a certain track 21. Thus, a position and an angle of the X-ray sensor 20 may be changed. Therefore, when the rotation arm 45 is placed at a certain position, then at least a part or the entire part of the X-ray sensor 20 may be placed within an irradiation range of an X-ray beam B emitted from the X-ray generator 30 and may face the X-ray generator 30 with the subject H being interposed therebetween.

Meanwhile, the X-ray generator 30 may also rotate on an axis A2 of the rotation arm 45 to an arrow direction d35 shown in a dotted line while being interlocked with the rotation of the rotation arm 45. Thus, the X-ray beam B may also be directed toward the subject H, and not toward the rotation axis A1.

When the second facing part 35 in which the X-ray generator 30 or the X-ray sensor is installed rotates to be directed toward the subject H along the rotation of the rotation arm 45, the X-ray sensor 20 that is movably installed may move along various tracks. Hereinafter, some examples of the various tracks are described. However, the configuration is not limited to the examples described herein.

In the embodiment to be described below, as the embodiment of FIGS. 3 and 4, the X-ray sensor 20 may be installed on the first facing part (not shown) and the X-ray generator 30 may be installed on the second facing part 35. The X-ray generator 30 may rotate on the rotation axis A2 such that a center of the X-ray beam is directed toward a center of the subject H even if the rotation arm 45 is rotated.

Figure 5:
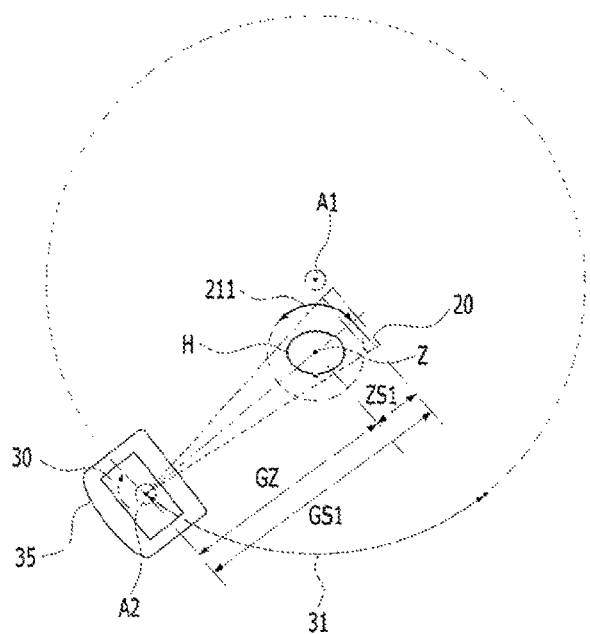
FIG. 5 is a schematic diagram showing a first track of a first facing part of a CT radiography device according to an embodiment of the present invention when a second facing part rotates.

FIG. 5 is a schematic diagram showing a first track of a first facing part of a CT radiography device according to an embodiment of the present invention when a second facing part rotates. When a position of the second facing part 35 is changed along a track 31, which has a circular arc form, of the X-ray generator 30 by the rotation of the rotation arm 45, as described above, the second facing part 35 rotates on a rotation axis A2 and a center of an X-ray beam emitted from the X-ray generator 30 may pass through the longitudinal axis Z of the subject H. The X-ray sensor 20 may move to face the center of the X-ray beam, and a direction of the X-ray sensor 20 may move to face the X-ray generator 30. Herein, the X-ray sensor 20 may move along a first track 211 which has a circular arc form having a radius, the radius being a distance ZS1 between the longitudinal axis Z of the subject H and the X-ray sensor 20.

When radiographing, a magnification power of a radiograph is determined by a ratio of a distance between the X-ray generator 30 and the subject H to a distance between the X-ray generator 30 and the X-ray sensor 20. In other words, GZ:GS1. When the X-ray generator 30 moves along a track 31 having a circular arc form of the X-ray generator 30, the GZ value is changed according to a position of the X-ray generator 30 and satisfies the following formula: GS1=GZ+ZS1. When the X-ray sensor 20 moves along a first track 211, the ZS1 becomes a constant. Then, the magnification power becomes GZ:GS1=1:1+(ZS1/GZ), and the magnification power is changed as the GZ value is changed (GZ is changed according to the position change of the X-ray generator 30 when radiographing). In a CT radiography device that obtains a CT image by reconfiguring multiple radiographs that are obtained at various angles, information of magnification power may be obtained while obtaining each radiograph since a magnification power of the multiple radiographs needs to be uniform. This information is used to calibrate the magnification powers before reconfiguring the CT image.

Figure 6:
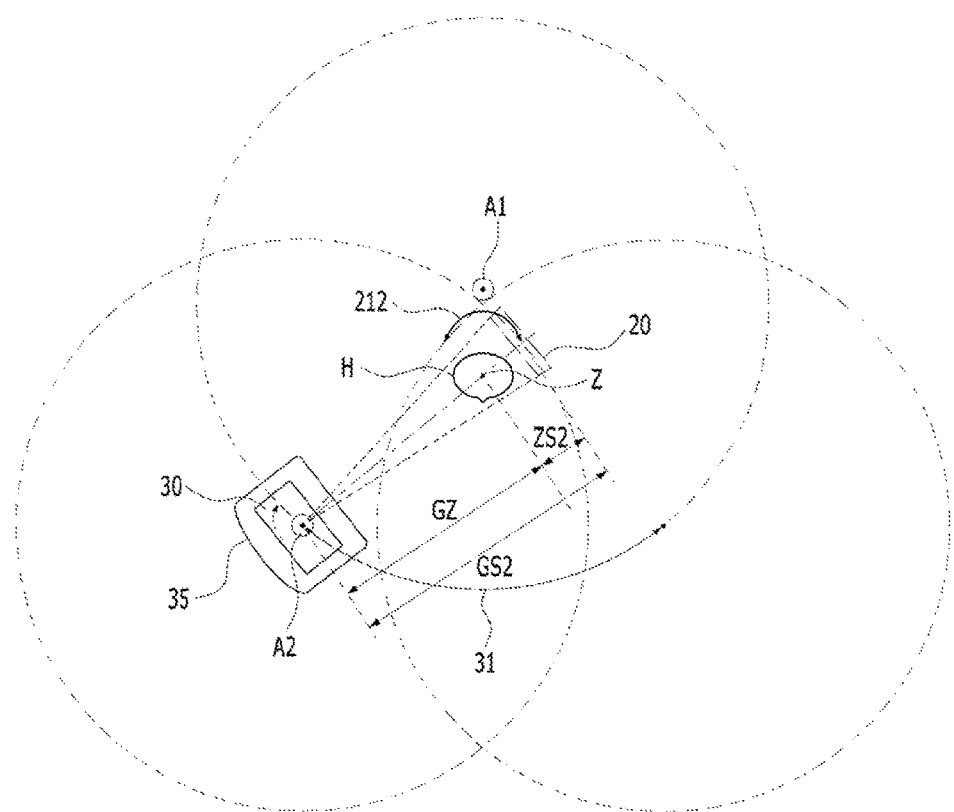
FIG. 6 is a schematic diagram showing a second track of the first facing part of the CT radiography device according to the embodiment of the present invention when a second facing part rotates.

FIG. 6 is a schematic diagram showing a second track of the first facing part of the CT radiography device according to the embodiment of the present invention when the second facing part rotates. The present embodiment is the same as the embodiment of FIG. 5 in that a movement of the second facing part 35, a track 31 of the X-ray generator 30, and a center of the X-ray sensor 20 move to face a center of the X-ray beam emitted from the X-ray generator 30, and the X-ray sensor 20 moves to face the X-ray generator 30. However, in the present embodiment, a characteristic of a second track 212 of the X-ray sensor 20, which shows a movement of a center of the X-ray sensor 20, is that a distance GS2 between the X-ray generator 30 and the X-ray sensor 20 is constantly maintained.

A magnification power of the CT radiography device according to the present embodiment is GZ:GS2, herein, the GS is a constant. When the X-ray generator 30 is placed on an extension of a rotation axis A1 of the rotation arm 45 and a longitudinal axis Z of the subject H, the GZ value becomes the minimum and the magnification power becomes the maximum. Alternatively, when the X-ray generator 30 moves to the left or the right from its position along a track 31 of the X-ray generator 30, the GZ value gradually becomes higher and the magnification power becomes lower. In the present embodiment, considering such changes, the magnification power may also be calibrated to reconfigure a CT image.

Figure 7:
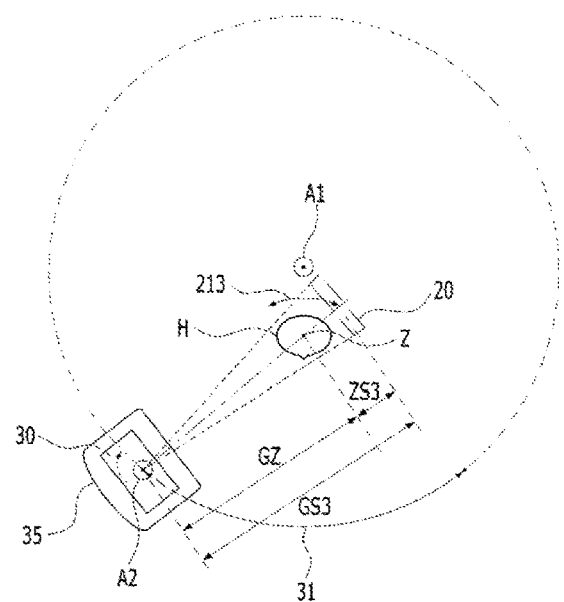
FIG. 7 is a schematic diagram showing a third track of the first facing part of the CT radiography device according to the embodiment of the present invention when a second facing part rotates.

FIG. 7 is a schematic diagram showing a third track of the first facing part of the CT radiography device according to an embodiment of the present invention when the second facing part rotates. The present embodiment is the same as the embodiment of FIG. 5 in that a movement of the second facing part 35, a track 31 of the X-ray generator 30, and a center of the X-ray sensor 20 move to face a center of the X-ray beam emitted from the X-ray generator 30, and the X-ray sensor 20 moves to face the X-ray generator 30. However, a third track 213 of the X-ray sensor 20, which shows a movement of a center of the X-ray sensor 20, may be designed in that a magnification power of a radiograph is constantly maintained even if the X-ray generator 30 moves in various positions within the track 31 thereof.

In order to constantly maintain the magnification power, in other words, GZ:GS3, when the GZ value is changed according to the position of the X-ray generator 30, then, the GS3 may be changed in the same manner as the ratio of change of the GZ value. In this case, when the X-ray generator 30 is placed on an extension of a rotation axis A1 of the rotation arm 45 and a longitudinal axis Z of the subject H, the GZ value becomes the minimum, and a distance ZS3 between the subject H and the X-ray sensor 20 also becomes the minimum. Therefore, at this position, there is a need that the X-ray sensor 20 should not be bumped into a surface of the subject H. In a CT radiography device according to the embodiment, magnification powers of radiographs obtained in various angles are constantly maintained. Thus, a CT image may be obtained by reconfiguring radiographs without calibrating the magnification powers.

Figure 8:
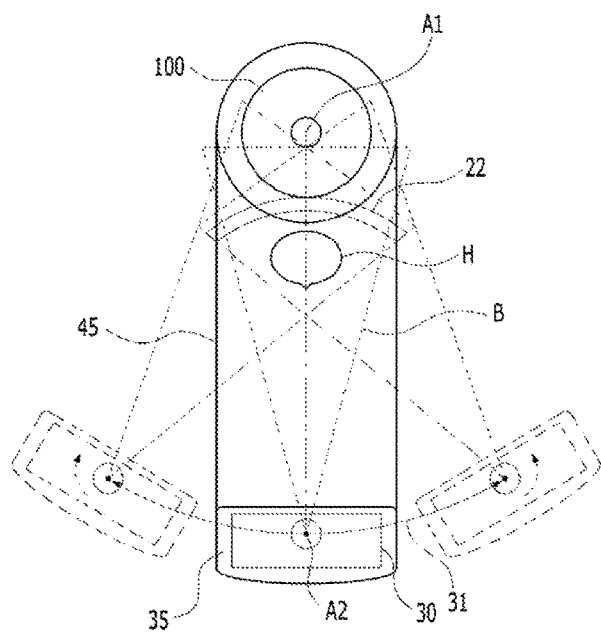
FIG. 8 is a schematic diagram showing a part of a track of a CT radiography device including a curved sensor according to an embodiment of the present invention.

FIG. 8 is a schematic diagram showing a part of a track of a CT radiography device including a curved sensor according to an embodiment of the present invention. This embodiment is different from the embodiments of FIGS. 3 and 4 in that a curved sensor 22 is used instead of the X-ray sensor 20 of a planar type. The curved sensor 22 may be installed such that at least a part of the curved sensor 22 faces the X-ray generator 30 with the subject H being interposed therebetween along a rotation angular range of the rotation arm 45. Alternatively, the curved sensor 22 may be installed to steadily cover the entire area in which the X-ray sensor 20 moves along the track 211.

Meanwhile, a first facing part 25 (Refer to FIG. 3) is not shown in FIGS. 4 to 8 such that shapes of the X-ray sensor 20 and 22 or moving tracks 21, 211, 212, and 213 thereof are clearly shown.

The invention claimed is:
1. A computed tomography (CT) radiography device, the CT radiography device comprising:
    a column;
    a first facing part provided on a first side of the column to face a subject and including one of an X-ray generator and an X-ray sensor;
    a rotation arm connected to the column and configured to rotate relative to the subject within at least a predetermined angular range; and
    a second facing part provided on a first end of the rotation arm to face the first facing part with the subject being interposed between the first facing part and the second facing part, and including a remaining one of the X-ray generator and the X-ray sensor,
    wherein the first facing part includes the X-ray sensor and the second facing part includes the X-ray generator, and
    wherein the X-ray sensor is configured to move within the first facing part along a rotation direction of the rotation arm such that at least a part of the X-ray sensor faces the X-ray generator within an X-ray irradiation range of the X-ray generator, with the subject being interposed therebetween.
2. The CT radiography device of claim 1, wherein the X-ray generator and the X-ray sensor are placed to arrange at least a part of the X-ray sensor facing the X-ray generator with the subject being interposed therebetween within an

X-ray irradiation range of the X-ray generator, while the rotation arm is placed within the predetermined angular range.

3. The CT radiography device of claim 1, wherein the X-ray sensor is configured to move along a track having a constant distance from the subject.

4. The CT radiography device of claim 1, wherein the X-ray sensor is configured to move along a track having a constant distance from the X-ray generator.

5. The CT radiography device of claim 1, wherein the X-ray sensor is configured to move along a track having a constant ratio of a distance between the X-ray generator and the subject and a distance between the X-ray generator and the X-ray sensor.

6. The CT radiography device of claim 1, wherein the X-ray sensor is a curved sensor configured to place at least a part of the X-ray sensor facing the X-ray generator, with the subject being interposed therebetween within a rotation angular range of the rotation arm.

7. The CT radiography device of claim 1, further comprising:
   a first driving part reciprocally rotating the second facing part within a predetermined angular range; and
   a second driving part simultaneously or alternatively operated with the first driving part and moving at least one of the first facing part and the second facing part in a direction of a longitudinal axis of the subject.

8. The CT radiography device of claim 7, wherein the first driving part is a rotary driving part connecting the column and the rotation arm and rotates the rotation arm on an axis of the column, and the second driving part is a linear driving part lifting and lowering at least one of the first facing part and the second facing part relative to the column.

* * * * *